United States Patent
Gale, Jr. et al.

(10) Patent No.: US 7,172,862 B2
(45) Date of Patent: Feb. 6, 2007

(54) FBL2-SPECIFIC AGENTS AS MODULATORS OF FLAVIVIRIDAE RNA REPLICATION

(75) Inventors: Michael J. Gale, Jr., Dallas, TX (US); Michael S. Brown, Dallas, TX (US); Joseph L. Goldstein, Dallas, TX (US); Chunfu Wang, Dallas, TX (US); Jin Ye, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 11/122,373

(22) Filed: May 4, 2005

(65) Prior Publication Data

US 2006/0252119 A1    Nov. 9, 2006

(51) Int. Cl.
  *C12Q 1/70* (2006.01)
  *C12P 21/06* (2006.01)
  *G01N 33/53* (2006.01)

(52) U.S. Cl. ............................ 435/5; 435/69.1; 435/7.1

(58) Field of Classification Search .................. 514/19, 514/18, 64, 2, 12, 44; 435/5, 6, 235.1
See application file for complete search history.

(56) References Cited

OTHER PUBLICATIONS

Wang et al. ("Identification of FBL2 As a Geranylgeranylated Cellular Protein Required for Hepatitis C Virus RNA replication," Molecular Cell, vol. 18 (pp. 425-434, May 13, 2005).*

* cited by examiner

*Primary Examiner*—Bruce R. Campell
*Assistant Examiner*—M. Franco Salvoza
(74) *Attorney, Agent, or Firm*—Richard Aron Osman

(57) ABSTRACT

Agents that modulate an interaction of an FBL2 protein with an NS5A or NS5B Flaviviridae protein in a mixture are identified by contacting the mixture with a candidate agent under conditions wherein but for the presence of the agent, the FBL2 protein and the Flaviviridae protein engage in a reference interaction; and detecting an agent-biased interaction. Flaviviridae replication is inhibited by contacting a Flaviviridae-infected cell with an FBL2-specific reagent; and detecting a resultant Flaviviridae replication inhibition.

20 Claims, No Drawings

FBL2-SPECIFIC AGENTS AS MODULATORS OF FLAVIVIRIDAE RNA REPLICATION

This work was supported by National Institute of Health Grants AI48325 and HL-20948. The U.S. government may have rights in any patent issuing on this application.

FIELD OF THE INVENTION

The field of the invention is modulation of the interaction of FBL2 with Flaviviridae NS5A or NS5B to reduce Flaviviridae RNA replication.

BACKGROUND OF THE INVENTION

Approximately 170 million people worldwide are infected persistently with hepatitis C virus (HCV) and these individuals account for most cases of chronic liver disease (Wasley and Alter, 2000). The public health impact of HCV is compounded by the low response rate to interferon (IFN)-based therapies, underscoring the need for new therapeutic strategies and new drug targets (McHutchison and Patel, 2002).

HCV is a single-stranded positive-sense RNA virus of the Flaviviridae family (Reed and Rice, 1998). The 9.6-kilobase HCV genome encodes a single polyprotein that is post-translationally processed into at least 10 structural and nonstructural (NS) proteins. Among the nonstructural (NS) proteins, NS3, NS4A, NS4B, NS5A, and NS5B are sufficient to support replication of the HCV RNA (Lohmann et al., 1999). Current studies support a model in which HCV infection results in assembly of the viral RNA and NS proteins into a replication complex that associates with cellular membranes, most likely a modified endoplasmic reticulum (Egger et al., 2002; El-Hage and Luo, 2003). The cellular proteins required for assembly and maintenance of the HCV replication complex are not known.

Inasmuch as native HCV cannot be efficiently propagated in cultured cells (Reed and Rice, 1998), genome-length and subgenomic HCV RNA replicons have been developed to facilitate the study of viral RNA replication. These HCV RNA replicon systems encompass either the entire HCV genome or only the NS3-5B protein coding region within a neomycin-selectable, bicistronic RNA. When introduced into human hepatoma (Huh7) cells, the HCV replicon RNA replicates autonomously on intracellular membranes (Lohmann et al., 1999; Egger et al., 2002).

We recently reported that HCV RNA replication in Huh7 cells can be disrupted by treatment with lovastatin, a drug that decreases the production of mevalonate by inhibiting 3-hydroxy-3-methylglutaryl CoA reductase (Ye et al., 2003). Mevalonate is a precursor of two hydrophobic prenyl groups, farnesyl (15 carbons) and geranylgeranyl (20 carbons), which are attached to various cellular proteins, anchoring them to membranes (Goldstein and Brown, 1990). Inhibition of HCV RNA replication by lovastatin was overcome by the addition of geranylgeraniol, but not farnesol, suggesting that HCV RNA replication requires one or more geranylgeranylated proteins (Ye et al., 2003). Kapadia and Chisari (2005) have subsequently reported similar results.

The role for a geranylgeranylated protein in HCV RNA replication is further supported by our additional finding that the replication could be blocked by an inhibitor of geranylgeranyl transferase I (GGTase-I) (Ye et al., 2003), an enzyme that transfers geranylgeranyl groups to many cellular proteins (Seabra et al., 1991; Zhang and Casey, 1996). GGTase-I attaches geranylgeranyl in thioether linkage to cysteine residues in proteins that contain a COOH-terminal Cys-A-A-X sequence (CAAX box), where C is cysteine, A is an aliphatic amino acid, and X is typically leucine (or rarely isoleucine, valine, or phenylalanine) (Reid et al., 2004).

Prenylated proteins can be labeled by incubating cultured cells with [$^3$H]mevalonate, which is enzymatically converted to [$^3$H]farnesyl pyrophosphate and [$^3$H]geranylgeranyl pyrophosphate, the donors in the protein prenylation reactions. Prenylated proteins within the $^3$H-labeled cell extracts can then be analyzed by SDS-PAGE and [$^3$H] autoradiography. Labeling with [$^3$H]mevalonate can be dramatically improved through the use of Met-18b-2 cells, a line of mutant Chinese hamster ovary (CHO) cells that takes up mevalonate at a very high rate (Faust and Krieger, 1987), owing to a gain-of-function point mutation in a monocarboxylate transporter (Garcia et al., 1994).

We used a combination of [$^3$H]mevalonate labeling, co-immunoprecipitation, and bioinformatic search to identify a geranylgeranylated host protein required for HCV RNA replication. We show that this protein, called FBL2, forms a specific complex with the HCV NS5A protein and that the FBL2-NS5A complex is crucial for HCV RNA replication. FBL2 is a previously identified protein that belongs to the family of F-box proteins and was originally cloned based on its homology to Skp2 (S-phase-kinase-associated protein 2), one of the best characterized proteins in this family (Ilyin et al., 1999). Like other F Box-containing proteins, FBL2 contains two distinct motifs: 1) an $NH_2$-terminal F-box that mediates the interaction between F-box proteins and the SCF E3 ubiquitin ligase complex (Cardozo and Pagano, 2004); and 2) 11 leucine-rich repeats involved in protein-protein interaction (Kobe and Kajava, 2001). Unlike other F-box proteins, FBL2 contains a potential geranylgeranylation sequence, CVIL, at the COOH-terminus. FBL2 is widely expressed in multiple tissues, including the liver (Ilyin et al., 1999).

SUMMARY OF THE INVENTION

The invention provides methods and compositions for modulating the functional interaction between an FBL2 protein with a Flaviviridae NS5A or NS5B protein. In one embodiment, the invention provides methods for identifying an agent that modulates an interaction of an FBL2 protein with a Flaviviridae NS5A or NS5B protein in a mixture, comprising the steps of (a) contacting the mixture with a candidate agent under conditions wherein but for the presence of the agent, the FBL2 protein and the Flaviviridae protein engage in a reference interaction; and (b) detecting an agent-biased interaction, wherein a difference between the reference and agent-biased interactions indicates that the agent modulates the interaction of the FBL2 protein and the Flaviviridae protein.

In particular embodiments, the Flaviviridae protein is from HCV, particularly HCV NS5A, or an NS5A protein having a carboxy-terminal truncation, and/or the FBL2 protein is an F-box truncated FBL2.

In particular embodiments, the mixture is within a cell expressing the Flaviviridae protein; within a cell transformed to express the FBL2 protein; or within a cell transformed to express the FBL2 and Flaviviridae proteins. Alternatively, the mixture may be cell-free.

In particular embodiments, the agent-biased interaction is detected directly, such as with a co-immunoprecipitation assay or a solid-phase binding assay; alternatively, the agent-biased interaction is detected inferentially or indirectly, such as in a viral RNA replication assay.

The invention also provides compositions comprising a mixture of an FBL2 protein and a Flaviviridae NS5A or NS5B protein, wherein at least one of the proteins is isolated, recombinantly-expressed, or in a predetermined amount. In various particular embodiments, the Flaviviridae protein is from HCV; the Flaviviridae protein is an NS5A protein having a carboxy-terminal truncation; the Flaviviridae protein is NS5A; the FBL2 protein has an F-box truncation; or the FBL2 protein is FBL2. In particular embodiments, the mixture is within a cell expressing the FBL2 and Flaviviridae proteins, particularly wherein the cell is transformed to express HCV NS5A.

The invention also provides methods of inhibiting Flaviviridae replication by modulating, particularly inhibiting FBL2 function. In one aspect, the method involves (a) contacting a Flaviviridae-infected cell with an FBL2-specific reagent, and (b) detecting a resultant Flaviviridae replication inhibition. Target Flaviviridae are dependent on FBL2 function, particular through a viral NS5A and/or NS5B protein. Applicable FBL2-specific reagents include FBL2-specific siRNA, PNA, antisense RNA, dominant negative FBL2 peptide, intrabody, NS5A or NS5B N-terminal peptide, and an agent identified or characterized in FBL2-NS5A/B interaction assays, such as described herein.

DETAILED DESCRIPTION OF SPECIFIC EMBODIMENTS OF THE INVENTION

In one aspect, the invention provides methods for identifying agents that modulate an interaction of an FBL2 protein with a Flaviviridae FBL2-interacting protein, particularly a NS5A or NS5B protein, in a mixture, comprising contacting the mixture with a candidate agent under conditions wherein but for the presence of the agent, the FBL2 protein and Flaviviridae protein engage in a reference interaction; and detecting an agent-biased interaction, wherein a difference between the reference and agent-biased interactions indicates that the agent is a modulator which modulates the interaction of the FBL2 protein and the Flaviviridae protein.

Preferred such Flaviviridae FBL2-interacting proteins derive from a hepacivirus such as HCV and hepatitis G virus (GBV), or a pestivirus such as classical swine fever virus (CSFV), border disease virus (BDV), and bovine viral diarrhea virus (BVDV). The Flaviviridae protein necessarily comprises a NS5A and NS5B sequence sufficient to specifically interact with human FBL2. Hence, the Flaviviridae protein can be a native NS5A, NS5B, or NSA protein, or can be or comprise a truncated portion thereof that retains ability to interact with FBL2 protein, such as an $NH_2$-terminal portion of HCV NS5A which can co-immunoprecipitate with FBL2. Hence, in particular embodiments, the FBL2-interacting Flaviviridae protein is an NS5A protein having a carboxy-terminal truncation of at least 50, 100 or 200 residues.

The FBL2 protein is preferably a mammalian FBL2 protein, preferably from a species susceptible to Flaviviridae infection such as cow, sheep, pigs, and humans. In a preferred embodiment the FBL2 protein is human FBL2 (see e.g. Ilyin et al, 1999; GenBank Accession No. Q9UKC9). The FBL2 protein can be a native FBL2, or can be or comprise a truncated portion thereof that retains ability to interact with a Flaviviridae NS5A or NS5B protein, such as an $NH_2$-terminal F-box truncated FBL2 which can coprecipitate with NS5A. Hence, in particular embodiments, the Flaviviridae NS5-interacting FBL2 protein is an FBL2 protein having an amino-terminal truncation of at least 50, 100 or 200 residues.

The mixture in which the FBL2 and Flaviviridae proteins interact can be in a cell in vitro or in situ, in a cell-fraction (e.g. membrane fraction), or essentially cell-free. In one embodiment, the mixture is within a Flaviviridae-infected cell, particularly an HCV or HCV-replicon infected cell. A variety of cells susceptible to Flaviviridae or Flaviviridae replicon infection are known in the art, including the human hepatoma cell lines Huh7 and Hep3B (see e.g. Tomassi et al, J. Virol. (2003) 77:11875–81), Madin-Darby bovine kidney cells (MDBK), and the pig kidney cell lines PK15 and SK-6. The cells may be transformed to express the FBL2 and/or Flaviviridae protein. In a preferred embodiment, the Flaviviridae is a hepacivirus, and the mixture is in a hepatoma cell.

FBL2-Flaviviridae protein interaction can be detected directly, indirectly, or inferentially using a variety of suitable assays known in the art including fluid and solid phase interaction assays (e.g. fluorescent polarization, enzyme-linked adsorption assays, etc.), cell-based interaction assays (e.g. transcriptional reporter assays such as two-hybrid assays, viral RNA replication assays, etc.), and animal-based assays (e.g. viremia assays), so long as the assay provides an indication of the targeted FBL2-Flaviviridae protein interaction. For example, with a co-immunoprecipitation assay a reduction or increase in the amount of coprecipitation of the Flaviviridae protein with the FBL2 protein in the presence of the agent compared to the amount of coprecipitation in the absence of the agent (i.e., reference interaction) indicates that the agent modulates the binding interaction of the FBL2 and Flaviviridae proteins. With a solid-phase binding assay the Flaviviridae protein may be bound to a solid-phase, and the amount of a labeled (e.g. biotinylated, radiolabeled, antibody-labeled etc.) FBL2 protein that binds to the Flaviviridae protein in the presence and absence of the agent is detected. Alternatively, the FBL2 protein may be bound to the solid phase, and the amount of a labeled Flaviviridae protein that binds to the FBL2 protein in the presence and absence of the agent is detected. Such solid-phase assays are particularly amenable for high-throughput screening of small molecule libraries to identify or validate novel antiviral agents.

The candidate agent can be any of a variety of agents to be tested for anti-Flaviviridae activity, such as an antisense agent (e.g. siRNA), an antigene agent (e.g. peptide nucleic acid (PNA), antisense DNA, morpholino, etc.), dominant negative peptide, intrabody, small molecule inhibitor, etc.

The invention also provides compositions comprising a mixture of an FBL2 protein and a Flaviviridae NS5A or NS5B protein, wherein one or both of the proteins is isolated, recombinantly-expressed, or in a predetermined amount. In various particular embodiments, the Flaviviridae protein is from HCV; the Flaviviridae protein is an NS5A protein having a carboxy-terminal truncation; the Flaviviridae protein is NS5A; the FBL2 protein has an F-box truncation; or the FBL2 protein is FBL2. In particular embodiments, the mixture is within a cell expressing the FBL2 and Flaviviridae proteins, particularly wherein the cell is transformed to express HCV NS5A.

The invention also provides assays of FBL2 prenylation which identify and characterize inhibitors of HCV replication that work by specifically blocking FBL2 geranylgeranylation. For example, in one robust and direct screen for inhibitors of FBL2 geranylation we use a biochemical/electrophoretic gel based-assay that measures FBL2 protein mobility shifts (mass shift) after treatment of cells with putative inhibitor compounds. Furthermore, this assay may be coupled to mass spectrometry analysis to quickly define the presence or absence of the geranylation.

Another aspect of the invention is a composition comprising an isolated cell transformed to express an FBL2 protein and expressing a NS5A or NS5B Flaviviridae protein. In one embodiment, the FBL2 protein is FBL2 or an FBL2 protein having an F-box truncation. In a further embodiment, the cell is infected with HCV or an HCV replicon, or is transformed to express the HCV protein. In one embodiment, the cell is transformed to express NS5A or an NS5A protein having a carboxy-terminal truncation.

The invention also provides methods of inhibiting Flaviviridae replication by inhibiting FBL2 function; for example, by specifically inhibiting FBL2 expression, geranylgeranylation, or Flaviviridae protein interaction. Applicable FBL2-specific reagents that reduce FBL2 functional expression include FBL2-specific siRNA, PNA, morpholino, antisense RNA, etc. FBL2-specific reagents that inhibit FBL2-Flaviviridae protein interaction include, inter alia, dominant negative F-box truncated FBL2 proteins, N-terminal NS5A peptides or mimetics, intrabodies specific to the CAAX box of FBL2 which prevent FBL2 geranylgeranylation and/or NS5A binding, and small molecule modulators of the FBL2 that binds FBL2 and reduce its interaction with the Flaviviridae protein or that bind a FBL2/Flaviviridae protein complex and inhibit Flaviviridae RNA replication. Additional reagents include specific inhibitors of FBL2 geranylgeranylation, such as are characterized in the disclosed FBL2 prenylation assays.

Target Flaviviridae are dependent on FBL2 function, particular through a viral NS5A protein. The method may include an antecedent step of detecting or confirming a target Flaviviridae infection, and/or the subsequent step of detecting a resultant Flaviviridae replication inhibition.

Applicable protocols for contacting the cell with the various FBL2-specific agents are known in the art and routinely optimized. For example, for target cells in vitro or in situ, known lentiviral and retroviral delivery methods can be used to deliver antisense agents, dominant negative proteins, and intrabodies. In addition, protocols currently used for administration of therapeutics in the treatment of HCV are readily adapted for administration of FBL2-specific-agents; for example, extant PEGylation techniques and administration protocols for interferon may be adapted to administer dominant negative FBL2, and Ribavirin treatment protocols may be adapted for FBL2-specific small molecule modulators, etc.

EXAMPLE 1

Identification of FBL2 as a Prenylated Cellular Protein that Associates with NS5A We performed experiments that indicated that a prenylated cellular protein of 50 kDa associates with NS5A. Because protein geranylgeranylation but not farnesylation is required for HCV replication (Ye et al., 2003) we used bioinformatic analysis to identify geranylgeranylated proteins having molecular masses in the range of 45 to 60 kDa. We identified 222 such proteins, and after further analysis, narrowed the list of the most likely candidates to three. To determine whether any of these three proteins binds to NS5A, we made plasmids encoding Myc-tagged versions of each protein. These plasmids were transfected into Huh7 cells together with a plasmid encoding NS5A preceded by Flag and HA epitope tags. Cell extracts were immunoprecipitated with anti-Flag beads to pull down NS5A and blotted with anti-HA and anti-Myc antibodies for detection of NS5A and the candidate geranylgeranylated proteins, respectively. Only one candidate protein, FBL2, clearly co-precipitated with NS5A.

To test whether FBL2 is prenylated, we created Met-18b-2 cells stably transfected with plasmids encoding $NH_2$-terminal Myc-tagged wild-type FBL2 or mutant FBL2 with the cysteine in the CAAX box (CVIL) changed to serine (C420S). These cells were labeled with [$^3$H]mevalonate for 16 hr, after which FBL2 was immunoprecipitated with rabbit polyclonal anti-Myc. The pellet and supernatant fractions of the immunoprecipitation were subjected to SDS-PAGE and analyzed by immunoblot with mouse monoclonal anti-Myc IgG-9E10 or by $^3$H-autoradiography. Immunoblot analysis showed that both wild-type and mutant FBL2 were expressed and precipitated at similar levels. Autoradiography revealed a radiolabeled band migrating at the same position as FBL2 in the immunoprecipitated pellet only when the cells were stably transfected with wild-type FBL2, but not FBL2(C420S). These data indicate that FBL2 is prenylated.

Since prenylation of proteins normally facilitates their membrane association, we compared the localization of wild-type FBL2 and the mutant FBL2 that cannot be prenylated. CHO-7 cells transfected with a plasmid encoding $NH_2$-terminal Myc-tagged wild-type FBL2 or mutant FBL2 (C420S) were treated either with GGTI-286, a drug that inhibits both geranylgeranylation and farnesylation, or with FPTI-III, a drug that inhibits only farnesylation (Ye et al., 2003). Cells were fractionated into cytosol and membrane fractions, and immunoblotted with monoclonal anti-Myc IgG-9E10. Almost all wild-type FBL2 was found in the membrane fraction, whereas the majority of mutant FBL2 (C420S) was in the cytosol fraction. Treatment with GGTI-286 but not FPTI-III altered the localization of wild-type FBL2 so that it was distributed equally in cytosol and membrane fractions. The effect of GGTI-286 was specific for wild-type FBL2 in that it did not change the subcellular localization of the mutant FBL2 that lacks a CAAX motif. This result demonstrates that geranylgeranylation enhances the association of FBL2 with membranes, and that this association can be inhibited by a drug inhibiting protein geranylgeranylation but not by one that specifically inhibits farnesylation.

Prenylated proteins, like FBL2, that contain leucine-terminated CAAX boxes, are almost always geranylgeranylated but not farnesylated (Reid et al., 2004). In vitro, the tetrapeptide CVIL corresponding to the CAAX box of FBL2 has previously been shown to be a substrate for GGTase-I but not farnesyltransferase (Roskoski and Ritchie, 1998). These data indicate that the prenyl group attached to FBL2 is geranylgeranyl.

To determine whether FBL2 forms a specific complex with NS5A, we performed co-immunoprecipitation experiments to examine the interaction between FBL2 and all HCV NS proteins. Huh7 cells were transfected with plasmids encoding Myc-tagged FBL2 and various HCV NS proteins, each tagged with Flag and HA epitope tags. The analyzed HCV proteins were NS3 and NS4A expressed from an NS34A polyprotein precursor, NS4AB polyprotein, NS4B, NS5A, and NS5B (Foy et al., 2003). Cell extracts were immunoprecipitated with anti-Flag beads to pull down the viral proteins and blotted with anti-HA and anti-Myc for detection of the viral proteins and FBL2, respectively. All viral proteins were precipitated quantitatively. FBL2 was clearly co-precipitated with NS5A, and a lesser amount was co-precipitated with NS5B (35% of that observed with NS5A). No co-precipitation was observed with NS3, NS4A, or NS4B. Similar results were obtained in two other experiments. Transfected FBL2 was also co-immunoprecipitated with NS5A encoded by cDNAs derived from two other sources, genotype 1a from a patient sample (Gale, Jr. et al., 1997; Kolykhalov et al., 1997) and genotype 1b from Huh7-HP replicon cells (Sumpter, Jr. et al., 2004). We conclude that FBL2 binds specifically to NS5A, and binds less efficiently to NS5B.

EXAMPLE 2

Structural Features Required for FBL2/NS5A Interaction

To determine the region of NS5A that mediates its interaction with FBL2, we constructed plasmids encoding Flag and HA-tagged versions of full length NS5A (1-448), the $NH_2$-terminal half (1-234), and the COOH-terminal half (235-448) of the protein. Each plasmid was transfected into Huh7 cells together with Myc-tagged FBL2. Cell extracts were immunoprecipitated with anti-Flag beads to pull down NS5A and blotted with anti-HA and anti-Myc for detection of NS5A and FBL2, respectively. Full length NS5A and the $NH_2$-terminal half of NS5A were co-precipitated with FBL2. The COOH-terminal half of NS5A was not co-precipitated with FBL2, even though it was expressed at a much higher level than the $NH_2$-terminal fragment.

To determine the components of FBL2 that are required for interaction with the $NH_2$-terminal half of NS5A, we made plasmids encoding the following proteins: $NH_2$-terminal Myc-tagged wild-type FBL2, FBL2 with its CAAX box mutated so that it cannot be geranylgeranylated (C420S), FBL2 with its $NH_2$-terminal F-box deleted (FBL2 (67-423)), and FBL2 with both its F-box deleted and its CAAX box mutated (FBL2 67-423, C420S). These plasmids were transfected into Huh7 cells together with a plasmid encoding Flag and HA-tagged NS5A. Cell extracts were immunoprecipitated with anti-Flag beads to pull down NS5A and blotted with anti-HA and anti-Myc for detection of transfected NS5A and FBL2, respectively. Wild-type and F-box deleted FBL2 were co-precipitated with NS5A. The C420S mutation abrogated binding when it was introduced into either the full length or F-box deleted FBL2. These results indicate that the geranylgeranylated CAAX box of FBL2 is required for its binding with NS5A, but the F-box is not required.

To detect the NS5A-FBL2 interaction in cells in which NS5A exists as a functional component of the HCV RNA replication complex, we transfected into Huh7-K2040 cells (Wang et al, 2003) plasmids encoding Flag and Myc-tagged wild-type FBL2 or the C420S mutant version that cannot be geranylgeranylated. Cell extracts were immunoprecipitated with anti-Flag beads to pull down FBL2 and then blotted with anti-Myc and anti-NS5A for detection of transfected FBL2 and endogenous NS5A, respectively. Since the NS5A is present in all cells but tagged FBL2 is present only in transfected cells, we carried out the immunoprecipitation only in experiments in which at least 80% of the cells were transfected. Transfection efficiency was estimated visually by transfecting plasmids encoding GFP. The endogenous NS5A was only co-precipitated with wild-type FBL2, but not the C420S mutant.

EXAMPLE 3

Overexpression of an F-Box Truncated FBL2 Inhibits HCV RNA Replication

FBL2(67-423), which lacks an F-box, is likely to be nonfunctional, yet it still binds to NS5A. We therefore considered the possibility that overexpression of FBL2(67-423) may inhibit HCV RNA replication in a dominant-negative fashion by sequestering NS5A and preventing it from interacting with endogenous functional FBL2. To test this hypothesis, we transfected plasmids encoding wild-type and various mutant versions of FBL2 into Huh7-K2040 cells that harbor the HCV RNA replicon. As described above, we included only those experiments in which at least 80% of the cells were transfected. Transfected wild-type FBL2 did not change the level of HCV RNA, whereas transfected FBL2 (67-423) reduced the level of HCV RNA by more than 80% in a dose-dependent manner. Importantly, transfected FBL2 (67-423; C420S), which cannot bind to NS5A, had no effect on HCV RNA levels. All wild-type and mutant versions of FBL2 were expressed at similar levels. Expression of wild-type and mutant versions of FBL2 did not result in general cellular toxicity as indicated by measurement of similar rates of total RNA and protein synthesis. These data demonstrate that the F-box truncated FBL2 is dominant-negative for HCV RNA replication and that this inhibitory action requires its prenylation. Alternative FBL2 N-terminal truncations including FBL2(50-423) and FBL2(100-423) similarly provide dominant-negative affects on HCV RNA replication.

To test the specificity of the dominant-negative effect of F-box truncated FBL2 we transfected wild-type and mutant versions of FBL2 into Huh7-WNV-2 cells, a line of Huh7 cells that harbor the West Nile virus replicon, which does not contain the genomic RNA sequence encoding NS5A (Brinton, 2002; Shi et al., 2002). Under conditions in which overexpression of FBL2(67-423) reduced the level of HCV RNA by 75% (mean of 3 experiments), there was no significant change in the level of West Nile virus replicon RNA even though the transfected FBL2s were expressed at similar levels in both Huh7-K2040 and Huh7-WNV-2 cells. These results confirm that the dominant-negative action of FBL2 is not caused by a nonspecific inhibition of RNA synthesis and indicate that the inhibition of HCV RNA replication depends on the presence of NS5A.

If the inhibition of HCV RNA replication by FBL2(67-423) is mediated through sequestration of NS5A, then overexpression of NS5A should saturate the FBL2(67-423), and the excess NS5A should bind to functional FBL2, thereby overcoming the inhibition. To this end, we cotransfected Huh7-K2040 cells with varying amounts of a plasmid encoding NS5A together with FBL2(67-423) and quantified the amount of HCV RNA. As a control, we cotransfected a plasmid encoding NS4B, a viral protein that does not bind to FBL2. Overexpression of NS5A, but not NS4B, overcame the dominant-negative action of FBL2(67-423) in a dose-dependent manner. Overexpression of NS5A did not increase HCV RNA levels in the absence of FBL2(67-423), indicating that NS5A becomes limiting only when it has been sequestered by the F-box deleted FBL2.

EXAMPLE 4

Anti FBL2 siRNA Reduces HCV RNA Replication

Further evidence that FBL2 is required for HCV RNA replication was obtained in experiments in which the level of FBL2 mRNA was reduced by transfection with duplex siRNA. An siRNA sequence targeting human FBL2 and having a sequence corresponding to positions 40-60 relative to the first nucleotide start codon, was transfected into Huh7-HP cells with TransMessenger transfection reagent (Qiagen) according to the manufacturer's protocol. In initial screening experiments, we failed to achieve greater than 50% knockdown of FBL2 in five of six HCV replicon cell lines that we examined, including Huh7-K2040 cells, even though the parental Huh7 cells responded to the same siRNA with >80% knockdown of FBL2 mRNA and even though the six cell lines expressed similar amounts of FBL2. The single HCV replicon cell line that consistently demonstrated FBL2 reduction was Huh7-HP cells (Sumpter, Jr. et al., 2004). We confirmed that these cells resemble the other HCV replicon cell lines in that HCV replication is inhibited by treatment with lovastatin (Ye et al., 2003) or an inhibitor of GGTase-I, GGTI-286. The NS5A derived from these cells interacts with FBL2. siRNA targeting FBL2 was and produced a 70% knockdown of FBL2 mRNA, an effect that was not observed when the cells were treated with a control siRNA containing 6 mismatched nucleotides. In the same experiment, HCV RNA was also reduced by 65% by the siRNA for FBL2, but not by the mismatch control siRNA. This knockdown was specific in that it did not significantly change the level of mRNAs produced by cellular genes, such as SCAP and Insig-1. The siRNA treatment did not produce general cellular toxicity, as assessed by total RNA and protein synthesis.

To test the specificity of the FBL2 siRNA effect on HCV RNA replication we transfected a plasmid containing a "wobble" mutant cDNA encoding FBL2 with three synonymous point mutations within the siRNA target sequence into Huh7-HP cells that had been previously treated with the siRNA duplexes described above. The "wobble" mRNA was not reduced by the RNAi treatment, and therefore it prevented the reduction in HCV RNA. These data confirm that the inhibition of HCV RNA replication by FBL2 RNAi is due to the reduction in mRNA encoding FBL2, and not due to "off target" effects of siRNA duplexes. Analogous experiments using Badin-Darby bovine kidney (MDBK) cells infected with BVDV and methodology adapted from Sun et al (J Virol. (2003) 77:6753-60) similarly demonstrate anti-FBL2 siRNA reduction of BVDV RNA replication.

EXAMPLE 5

Adenovirus Expressing Dominant Negative FBL2 Decreases HCV Serum Titer in HCV Mouse Model Using methodology adapted from Hsu et al (2003) Nat Biotechnol. 21:519–25, a mouse model for HCV infection is engineered to express dominant-negative FBL2. Sequence encoding dominant negative FBL2 (dnFBL2) with a FLAG epitope tag is subcloned into the pShuttle vector (Clontech, Palo Alto, Calif.) and recombinant adenovirus is isolated and amplified following manufacturer protocols. Alb-uPA transgenic mice (Mercer et al (2001) Nat. Med 7:927–933) are inoculated intraperitoneally with HCV from the serum of chronically infected patients. The HCV-titers of the mice are determined two weeks later, and the mice are inoculated with $10^9$ PFU of nonreplicating adenovirus that express the dnFBL2. In addition to the experimental animals, controls consist of HCV-infected mice that are injected with nonreplicating adenovirus that does not contain the gene for dnFBL2 and uninfected mice that are injected with non-replicating adenovirus that expresses dnFBL2. Mice receive repeated adenovirus injections at 3 and 6 days after the initial adenovirus injection. Liver biopsies are taken at 5 and 10 days after adenovirus injection and are assayed for expression of dnFBL2 expression using a FLAG antibody. Serum samples are collected at 0, 2, 5, 10, 14, 21, and 28 days after the initial adenovirus injections and HCV RNA titers are determined. Reduction in HCV RNA titer in experimental, but not control animals, demonstrates efficacy of dnFBL2 gene therapy for treatment of HCV.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims

REFERENCES

Brinton, M. A. (2002) Annu. Rev. Microbiol. 56:371–402.
Cardozo, T. and Pagano, M. (2004) Nat. Rev. Mol. Cell Biol. 5:739–751.
Egger et al (2002) J. Virol. 76:5974–5984.
El-Hage, N. and Luo, G. (2003) J. Gen. Virol. 84:2761–2769.
Faust, J. and Krieger, M. (1987) J. Biol. Chem. 262: 1996–2004.
Foy et al (2003) Science 300:1145–1148.
Gale et al (1997) Virology 230:217–227.
Garcia et al (1994) Cell 76:865–873.
Goldstein, J. L. and Brown, M. S. (1990) Nature 343: 425–430.
Ilyin et al (1999) FEBS Lett. 459:75–79.
Kapadia, S. B. and Chisari, F. V. (2005) Proc. Natl. Acad. Sci. USA 102:2561–2566.
Kobe, B. and Kajava, A. V. (2001) Curr. Opin. Struct. Biol. 11:725–732.
Kolykhalov et al (1997) Science 277:570–574.
Lohmann et al (1999) Science 285:110–113.
McHutchison, J. G. and Patel, K. (2002) Hepatology 36:S245–S252.
Reed, K. E. and Rice, C. M. (1998) In Hepatitis C Virus, H. W. Reesink, ed., pp. 55–84.
Reid et al (2004) J. Mol. Biol. 343:417–433.
Roskoski, R. Jr. and Ritchie, P. (1998) Arch. Biochem. Biophys. 356:167–176.
Seabra et al (1991) Cell 65:429–434.
Shi et al (2002) Virology 296:219–233.
Sumpter et al (2004) J. Virol. 78:11591–11604.
Wang et al (2003) J. Virol. 77:3898–3912.
Wasley, A. and Alter, M. J. (2000) Semin. Liver Dis. 20:1–16.
Ye et al (2003) Proc. Natl. Acad. Sci. USA 100:15865–15870.
Zhang, F. L. and Casey, P. J. (1996) Annu. Rev. Biochem. 65:241–269.

What is claimed is:

1. A method for identifying an agent that inhibits an interaction of a mammalian FBL2 protein with an HCV NS5A or NS5B protein in a mixture wherein each said protein is isolated, recombinantly-expressed, or in a predetermined amount, comprising the steps of:

contacting the mixture with a candidate agent under conditions wherein but for the presence of the agent, the FBL2 protein and the HCV protein engage in a reference specific interaction; and detecting an agent-biased specific interaction, wherein a reduced agent-biased interaction as compared with the reference interaction indicates that the agent inhibits the interaction of the FBL2 protein and the HCV protein.

2. The method of claim 1 wherein the HCV protein is HCV NS5A.

3. The method of claim 1 wherein the HCV protein is NS5A, and the NS5A protein has a carboxy-terminal truncation.

4. The method of claim 1 wherein the FBL2 protein is an F-box truncated FBL2.

5. The method of claim 1, wherein the mixture is within a cell expressing the HCV protein.

6. The method of claim 1 wherein the mixture is within a cell transformed to express the FBL2 protein.

7. The method of claim 1 wherein the mixture is within a cell transformed to express the FBL2 and HCV proteins.

8. The method of claim 1 wherein the mixture is cell-free.

9. The method of claim 1 wherein the agent-biased interaction is detected directly with a co-immunoprecipitation assay or a solid-phase binding assay.

10. The method of claim 1 wherein the agent-biased interaction is detected indirectly in a viral RNA replication assay.

11. The method of claim 1 wherein the FBL2 protein is an F-box truncated FBL2 consisting of residues 67–423 of FBL2.

12. The method of claim 1 wherein the FBL2 protein is an F-box truncated FBL2 consisting of residues 100–423 of FBL2.

13. The method of claim 1 wherein the HCV protein is an NS5A protein having a carboxy-terminal truncation and consisting of the $NH_2$ terminal 234 residues of NS5A.

14. The method of claim 1 wherein the FBL2 protein is an F-box truncated FBL2 consisting of residues 67–423 of FBL2, and the HCV protein is an NS5A protein having a carboxy-terminal truncation and consisting of the $NH_2$ terminal 234 residues of NS5A.

15. The method of claim 14, wherein the mixture is within a cell expressing the HCV protein.

16. The method of claim 14 wherein the mixture is within a cell transformed to express the FBL2 protein.

17. The method of claim 14 wherein the mixture is within a cell transformed to express the FBL2 and HCV proteins.

18. The method of claim 14 wherein the mixture is cell-free.

19. The method of claim 14 wherein the agent-biased interaction is detected directly with a co-immunoprecipitation assay or a solid-phase binding assay.

20. The method of claim 14 wherein the agent-biased interaction is detected indirectly in a viral RNA replication assay.

* * * * *